United States Patent
Zhu et al.

(10) Patent No.: US 12,222,550 B2
(45) Date of Patent: Feb. 11, 2025

(54) LIGHT SCATTERING PATCH DEVICE AND PREPARATION METHOD THEREOF

(71) Applicant: ZHEJIANG UNIVERSITY, Hangzhou (CN)

(72) Inventors: Yang Zhu, Hangzhou (CN); Lei Zhang, Hangzhou (CN); Yao Tang, Hangzhou (CN); Kaicheng Deng, Hangzhou (CN); Liyin Shen, Hangzhou (CN)

(73) Assignee: ZHEJIANG UNIVERSITY, Wujiang (CN)

( * ) Notice: Subject to any disclaimer, the term of this patent is extended or adjusted under 35 U.S.C. 154(b) by 0 days.

(21) Appl. No.: 18/713,209

(22) PCT Filed: Aug. 2, 2022

(86) PCT No.: PCT/CN2022/109643
§ 371 (c)(1),
(2) Date: May 24, 2024

(87) PCT Pub. No.: WO2023/103420
PCT Pub. Date: Jun. 15, 2023

(65) Prior Publication Data
US 2024/0418936 A1 Dec. 19, 2024

(30) Foreign Application Priority Data
Dec. 9, 2021 (CN) .......................... 202111497836.3

(51) Int. Cl.
*G02B 6/26* (2006.01)
*G02B 6/25* (2006.01)
(Continued)

(52) U.S. Cl.
CPC .............. *G02B 6/262* (2013.01); *G02B 6/25* (2013.01); *G02B 6/4203* (2013.01);
(Continued)

(58) Field of Classification Search
CPC .......... G02B 6/0008; G02B 6/26; G02B 6/42; G02B 6/122; G02B 6/132; G02B 6/136;
(Continued)

(56) References Cited

U.S. PATENT DOCUMENTS

| 2006/0018596 A1* | 1/2006 | Loebel | A61B 18/22 385/38 |
| 2010/0210911 A1* | 8/2010 | Shimotsu | A61B 1/07 600/178 |

(Continued)

FOREIGN PATENT DOCUMENTS

| CN | 1997323 A | 7/2007 |
| CN | 101716485 A | 6/2010 |

(Continued)

OTHER PUBLICATIONS

Yan Xiao, et al., A highly stretchable bioelastomer prepared by UV curing of liquid-like poly (4-methyl-ε-caprolactone) precursors, Journal of Materials Chemistry B, 2013, pp. 1-10.

(Continued)

*Primary Examiner* — Michael P Mooney
(74) *Attorney, Agent, or Firm* — Bayramoglu Law Offices LLC (57) ABSTRACT

A light scattering patch device and preparation method thereof is disclosed. The light scattering patch device is composed of a patch, an air gap, and a tapered optical fiber; the patch is a transparent patch; a refractive index of the patch is greater than a refractive index of a biological tissue; a tip, a tapered transition zone and a partial unstretched zone of the tapered optical fiber are embedded in the patch, and the air gap is formed between the tip and the tapered transition zone of the tapered optical fiber and the patch. The method of preparing the light scattering patch device comprises: first preparing the tapered optical fiber, then performing hydrophobic modification on the surface of the tapered (Continued)

optical fiber; placing the tapered optical fiber in an uncured polymer and curing the uncured polymer, and pulling the unstretched part; connecting the unstretched part of the tapered optical fiber.

15 Claims, 3 Drawing Sheets

(51) Int. Cl.
- *G02B 6/42* (2006.01)
- *F21V 8/00* (2006.01)
- *G02B 6/122* (2006.01)
- *G02B 6/30* (2006.01)

(52) U.S. Cl.
CPC .......... *G02B 6/0008* (2013.01); *G02B 6/1228* (2013.01); *G02B 6/305* (2013.01)

(58) Field of Classification Search
CPC .... G02B 6/1228; G02B 6/12004; G02B 6/14; G02B 6/305; A61B 18/20; A61B 18/22; A61N 5/067
See application file for complete search history.

(56) References Cited

U.S. PATENT DOCUMENTS

| | | | |
|---|---|---|---|
| 2015/0126982 A1 | 5/2015 | Neuberger | |
| 2017/0079717 A1 | 3/2017 | Walsh et al. | |

FOREIGN PATENT DOCUMENTS

| | | |
|---|---|---|
| CN | 101846765 A | 9/2010 |
| CN | 111948757 A | 11/2020 |
| CN | 114137663 A | 3/2022 |

OTHER PUBLICATIONS

Sedat Nizamoglu, et al., Bioabsorbable polymer optical waveguides for deep-tissue photomedicine, Nature Communications, 2016, pp. 1-7, 19:7:10374.

Kiwoon Kwon, et al., Enhancement of light propagation depth in skin: cross-validation of mathematical modeling methods, Lasers Med Sci., 2009, pp. 605-615, vol. 24.

Guosong Hong, et al., Multifunctional in vivo vascular imaging using near-infrared II fluorescence, Nature Medicine, 1841-1848, vol. 18 No. 12.

Steven L Jacques, Corrigendum: Optical properties of biological tissues: a review, Physics in Medicine and Biology, 2013, pp. 5007-5008, vol. 58.

Myunghwan Choi, et al., Light-guiding hydrogels for cell-based sensing and optogenetic synthesis in vivo, Nature Photonics, 2013, pp. 1-8.

Shujuan Gao, The propagation properties of optical fiber tapers and relative characteristics, Zhejiang University, 2008, pp. 1-60.

\* cited by examiner

LIGHT SCATTERING PATCH DEVICE AND PREPARATION METHOD THEREOF

CROSS REFERENCE TO RELATED APPLICATIONS

This application is a national stage entry of International Application No. PCT/CN2022/109643, filed on Aug. 2, 2022, which is based upon and claims foreign priority to Chinese Patent Application No. 202111497836.3, filed on Dec. 9, 2021, the entire contents of which are incorporated herein by reference.

TECHNICAL FIELD

The present invention belongs to the technical field of patch devices, and more particularly, relates to a light scattering patch device and preparation method thereof.

BACKGROUND

For a long time, optical fibers and waveguide devices have been widely used in fields such as optical fiber communications, remote sensing, and organ chips. With the development of optical technology towards medical applications, the interaction between light and biological substances has demonstrated huge potential for biomedical applications, such as laser surgery, phototherapy, sensing, imaging, etc. However, the optical loss caused by the scattering and absorption of light by biological tissues severely limits the application of visible light and near-infrared light in the body, and the data proves that the intensity of visible light and near-infrared light is reduced to less than 1/e level (37%) after penetrating 1 mm in soft tissues, which total penetration depth is very limited (<3 mm). At the same time, the limitation of light intensity in human tissues (4 W cm-2) makes the application of transdermal light transmission of external lighting very limited in human body, as can be seen in Reference 1 (*Enhancement of light propagation depth in skin: cross-validation of mathematical modeling methods. Lasers Med Sci* 24, 605-615 (2009)), Reference 2 (*Multifunctional in vivo vascular imaging using near-infrared II fluorescence. Nat Med* 18, 1841-1846 (2012)), Reference 3 (*Corrigendum: Optical properties of biological tissues: a review. Physics in Medicine and Biology* 58, 5007-5008 (2013)) and Reference 4 (*Light-guiding hydrogels for cell-based sensing and optogenetic synthesis in vivo. Nat Photonics* 7, 987-994 (2013)).

In medical applications, the endoscope can enter the human body in a minimally invasive manner and provide lighting at specific parts. However, the existing endoscope is only used for specific parts with large cavities, meanwhile, the large size of the endoscope makes it very limited in application and unsuitable for long-time continuous operation. Implantable light sources, such as light-emitting diodes, cell-based lasers, miniature photoelectric upconversion devices, and nanoparticles, have been developed and proven useful in biomedical applications. However, problems in their preparation process and biocompatibility severely limit the application of these implantable light sources in biological applications.

In recent years, the development of implantable optical fibers has provided a feasible concept, due to good flexibility and small size, it is possible to transmit light for therapy or sensing to a respective deep tissue in a non-invasive or minimally invasive way to overcome penetration limitations and spatial obstacles. Existing implantable optical fibers include flat-end optical fibers and tapered optical fibers, and the tapered optical fiber is developed to overcome the problem that the small divergence angle of emergent light of the flat-end optical fiber only can be applied to certain scenes (such as optogenetic control in the brain); in order to modulate the irradiation range of light, the tapered optical fiber is usually manufactured by an etching method and a stretching method.

Figure 9:
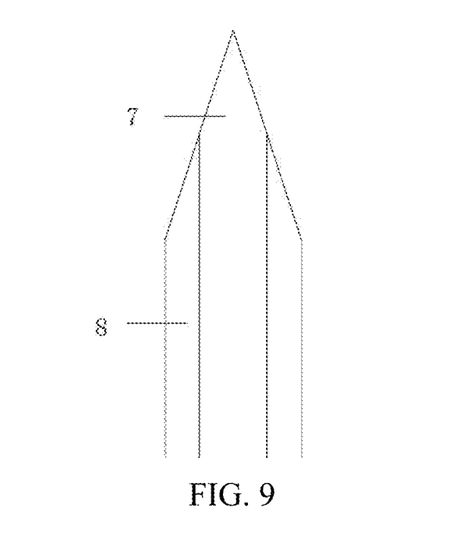
FIG. 9 is a schematic structural diagram of the tapered optical fiber made by the etching method.

The tapered optical fiber made by the etching method is mainly used to photostimulate biological tissues or collect fluorescence in tissues to monitor neural activity. The tapered optical fiber prepared by the etching method does not change the refractive index distribution of the optical fiber, only etching the optical fiber into a tapered shape by removing the excess part, as shown in FIG. 9, and the tapered optical fiber made by the etching method includes an etched optical fiber core 7 and an etched optical fiber cladding 8. The tapered area of the etched optical fiber is usually conical, and the cross-sectional radius has an approximately linear relationship with the distance from the tip to the cross-section, and in areas where the cross-sectional radius is smaller than the radius of the original fiber core, all the cladding materials are etched away and only the tapered fiber cores are left, so that when the light is transmitted to the half of the tapered area near the tip, part of the light is emitted through the side wall of the fiber core exposed to the environment, while part of the light continues to be transmitted forwards through total reflection until emergent. Whether it is scattering or collection during light stimulation, the input and output of light from the tapered optical fiber made by the etching method mainly pass through the side wall of the tip of the tapered area, so the tapered optical fiber has to be pierced into biological tissues during deep illumination, which will cause certain damage. In addition, the irradiation range of the tapered optical fiber made by this method is still limited, and the length of the tapered area of the tapered optical fiber is in the order of millimeters to centimeters, making it difficult to further reduce the size of the device; during operation, the tapered optical fiber is directly exposed to the biological environment, which is relatively fragile and susceptible to contamination, and the port of the optical fiber is relatively fragile and sensitive, so that the complex physiological environment in the body will seriously affect the service life of the optical fiber and the waveguide as well as the efficiency of their light guidance.

SUMMARY

The purpose of the invention is to solve the problems of tapered optical fibers prepared by the etching method in the prior art, and to provide a light scattering patch device and preparation method thereof.

To this end, the technical schemes of the invention are as follows:

A light scattering patch device, comprising a patch, an air gap, and a tapered optical fiber;

wherein the patch is a transparent patch, for conducting light, it is sufficient to choose a material transparent to the light according to the light to be conducted, which can be judged by common sense;

wherein a refractive index of the patch is greater than a refractive index of a biological tissue (generally the refractive index of biological tissue is less than 1.42);

wherein a stretched part, a tapered transition zone and a partial unstretched zone of the tapered optical fiber are embedded in the patch, and the air gap is formed between the stretched part and the tapered transition zone of the tapered optical fiber and the patch;

wherein a relationship between a cross-sectional radius F(z) of the tapered optical fiber and a distance z from a cross-section to the tip of the tapered optical fiber satisfies a function 1; assuming that a length of the tapered transition zone is d, and the function 1 is:

$$F(z)=62.3-56.36\times\exp(-((135.8\times(z/d)+16.18)/65.81)^2)+0.6324\times\exp(-((135.8\times(z/d)+0.5469)/0.1508)^2)+1.103\times\exp(-((135.8\times(z/d)+24.78)/-0.02043)^2)-12.1\times\exp(-((135.8\times(z/d)-13.07)/-22.32)^2);$$

wherein the cross-sectional radius F(z), the distance z from the cross-section to the tip of the tapered optical fiber, and the length d of the tapered transition zone are all in the unit of μm.

This formula is a formula related to the length of the tapered transition zone. The cross-sectional radius F(z) first increases and then remains unchanged, specifically: it gradually increases from 1-2 μm to 125 μm at the tip and then stabilizes without changing.

The following preferred technology program is presented to give a detailed description for this invention:

The said light scattering patch device, wherein a tip diameter of the tapered optical fiber is less than 3 μm; wherein the tip diameter directly affects the divergence angle of the tapered optical fiber, the smaller the tip diameter, the larger the divergence angle, and the invention requires light with a larger divergence angle, so the tip diameter is set to less than 3 μm;

wherein the length d of the tapered transition zone of the tapered optical fiber is 250 μm-300 μm; wherein the tapered transition zone is defined as the zone between the tip and the unstretched part of the tapered optical fiber; there is no requirement for the length of the unstretched part, which can be as long or as short as needed for use;

wherein a shape of a contact surface of the air gap and the patch is the same as a shape of a contact surface of the air gap and the tapered optical fiber, and the contact surface of the air gap and the tapered optical fiber is a contour surface of the tip and the tapered transition zone of the tapered optical fiber; wherein the air gap is obtained by pulling the optical fiber out from the patch along the axis for a certain distance, so the contact surface of the air gap and the tapered optical fiber is the same as the contour surface of the tip and the tapered transition zone of the tapered optical fiber, which also satisfies the relationship of function 1;

wherein a maximum distance between the contact surface of the air gap and the patch, and the contact surface of the air gap and the tapered optical fiber is 3-20 μm;

wherein a divergence angle of the light scattering patch device is 126°-130°. The test method for the divergence angle is as follows: placing the patch in a fluorescent solution with a refractive index of 1.40 (to simulate the working environment), then passing the pump light into the device, emitting the divergent light to excite the fluorescence, and the area where fluorescence is generated corresponds to the coverage area of the divergent light. Taking a photo, using image processing to calculate the angle between the two edges of the luminous area (and the boundary line of the dark area), that is, the divergence angle.

The invention also provides a method of preparing the light scattering patch device, comprises the following steps:

(1) stripping a protective layer from a standard multimode optical fiber with a core diameter of 62 μm;

(2) preparation of tapered optical fiber: preparing the tapered optical fiber by a melt stretching method;

wherein the melt stretching method refers to using a single-core optical fiber fusion splicer (the model can be selected as Fujikura 80S+ optical fiber fusion splicer), and setting the single-core optical fiber fusion splicer to [MM-MM/Taper splice] mode and a certain stretching distance to break a standard communication optical fiber;

in the prior art, the advanced optical fiber fusion splicer (such as Ericsson FSU995PM) has its own procedure for stretching tapered optical fibers, however, the optical fiber stretched by this method has a long transition zone, the tip is blunt and the diameter is large, which does not have a divergence effect; the present invention uses the single-core optical fiber fusion splicer to prepare the tapered optical fiber for the first time, specifically by increasing the set of stretching distance, to break the optical fiber and prepare the tapered optical fiber;

during melt stretching, the structure of the desired tapered optical fiber can be formed according to the set of stretching distance, and the specific method is: after setting the stretching distance (or stretching at a certain value of the extension length), adjusting the discharge power of the fusion splicer, so that when the stretching stops, the optical fiber is broken into a cone, thereby obtaining the tapered optical fiber;

(3) surface treatment of the tapered optical fiber: performing hydrophobic modification on the surface of the tapered optical fiber obtained in step (2); through the surface treatment of the tapered optical fiber, a chemically modified hydrophobic layer is formed on the surface of the tapered optical fiber, which can be pulled outward from the patch along the central axis of the tapered optical fiber to obtain the air gap without damaging the patch;

(4) placing the tapered optical fiber obtained in step (3) in an uncured polymer and curing the uncured polymer, and then pulling the unstretched part of the tapered optical fiber outwards by a certain distance along the central axis of the tapered optical fiber to form the air gap;

wherein the uncured polymer is a poly(4-methyl-ε-caprolactone) (PMCL) modified by double bonds at both ends, a polydimethylsiloxane (PDMS), a polylactic acid (PLA), a poly(lactic-co-glycolic acid) (PLGA) modified by double bonds at both ends, or a polyethylene glycol (PEGDA) modified by double bonds at both ends;

Since the material can be poured, before pulling the optical fiber, the tapered optical fiber and the patch are tightly attached without gaps, meanwhile, the patch is more flexible than the optical fiber (the material of the patch has better elasticity and flexibility while the tapered optical fiber is more brittle), and there is a hydrophobic layer on the surface of the tapered optical fiber, which can be easily pulled out of the patch; the optical fiber can only be pulled backward along the axis, the only thing that can be controlled is the pulling distance, after the optical fiber is pulled along the axis, a corresponding air gap will be formed. The thickness of the air gap can be controlled by controlling the pulling distance.

(5) connecting the unstretched part of the tapered optical fiber obtained in step (4) that is not embedded in the patch to a light source through a standard optical fiber adapter, to form the light scattering patch device, and turning on the light source can illuminate the entire fiber patch.

The following preferred technology program is presented to give a detailed description for this invention:

The said method of preparing the light scattering patch device, wherein the specific process of step (3) is as follows: placing the tapered optical fiber obtained in step (2) in a vacuum dryer under an atmosphere containing trichloro(1H, 1H, 2H, 2H-tridecafluoro-n-octyl) silane; the operation can be as follows: placing the tapered optical fiber obtained in step (2) and a petri dish containing 100 μL of trichloro(1H, 1H, 2H, 2H-tridecafluoro-n-octyl) silane in the vacuum dryer at the same time, in which the tapered optical fiber and the petri dish are independent of each other and are not in direct contact with each other; and vacuumizing until an air pressure is less than 0.1 MPa, then placing at room temperature for 8 hours;

wherein the certain distance in step (4) is 5-40 μm.

The principle of the present invention is as follows:

Problems with tapered optical fibers produced with etching method in the prior art include: ① the input and output of light from the tapered optical fiber mainly pass through the side wall of the tapered area, so the tapered optical fiber has to be pierced into biological tissues during deep illumination, which will cause certain damage; ② the irradiation range of the tapered optical fiber is still limited (the divergence angle does not exceed) 40°); ③ the length of the tapered area of the tapered optical fiber is in the order of millimeters to centimeters, making it difficult to further reduce the size of the device; ④ during operation, the tapered optical fiber is directly exposed to the biological environment, which is relatively fragile and susceptible to contamination; the port of the optical fiber is relatively fragile and sensitive, so that the complex physiological environment in the body will seriously affect the service life of the optical fiber and the waveguide as well as the efficiency of their light guidance.

The light scattering patch device of the invention can solve the problems existing in the tapered optical fiber prepared by the etching method in the prior art, the specific reasons are as follows:

(1) the patch structure enables the device to be attached to the surface of the biological tissue without causing damage to the tissue;

(2) the tapered optical fiber is pulled by the optical fiber fusion splicer, in the tip area of the tapered optical fiber, the diameter of the optical fiber decreases rapidly, and after the light in multiple modes is transmitted into the tip, it no longer meets the transmission conditions and radiates outward, since the size of the tip is small enough, resulting in obvious diffraction effect, and finally, the tip has a large scattering angle (126°-130°), so that the device has a relatively large irradiation range;

the dispersion angle of light emitted from the optical fiber is related to the refractive index of the environment where the optical fiber is located, the greater the refractive index of the environment, the smaller the divergence angle of the light (the numerical aperture of the optical fiber is certain, $NA = n \times \sin\theta$, the larger the n, the smaller the θ); when the patch directly covers the tapered optical fiber (i.e., there is no air gap and the two are in direct contact), the refractive index of the environment at the emergence end is larger, so that the divergence angle is reduced compared with the tapered optical fiber in the air; the invention performs surface treatment on the tapered optical fiber, and constructs an air gap between the tapered optical fiber and the patch, after the light is emitted from the tip at a larger divergence angle, it is incident into the patch and refracted at the same time, so that the final divergence angle rises to 130°, while the divergence angle of the patch without air gap is only 45°;

the emergent light from the tapered optical fiber is refracted at the interface between the air gap and the patch material, which increases its irradiation area in one step in the direction parallel to the patch surface, and at the same time increases the component of light propagating radially to the optical fiber;

(3) the optical fiber fusion splicer is used to stretch the tapered optical fiber, its welding electrode discharges, and the arc heating area is small so the temperature rises quickly; the area of it melting optical fibers is much smaller than the area of oxyhydrogen flame or carbon dioxide laser melting optical fibers, so that the length of the tapered area of the stretched tapered optical fiber is shorter;

(4) the a stretched part, a tapered transition zone and a partial unstretched zone of the tapered optical fiber are embedded in the patch to protect the tapered optical fiber from the interference of complex environment inside the body, which significantly increases the stability, mechanical strength and resistance to electromagnetic interference of the tapered optical fiber; at the same time, due to the existence of the air gap, there is a certain distance of buffer between the tapered optical fiber and the patch, and the friction between the tapered optical fiber and the patch can be reduced; taking the stretching distance of 40 μm as an example, when the patches on both sides of the tip are displaced in the radial direction of the tapered optical fiber to reach more than 15 μm, the tapered optical fiber will come into contact with the patches, which can significantly increase the degree of bendability and the number of bends of the device, and increase the service life of the device. Therefore, the light scattering patch device of the invention can protect the tapered optical fiber from the interference of external environment and improve the stability and operability of the device.

Benefits:

(1) The said light scattering patch device of the invention, comprises the patch, the air gap, and the tapered optical fiber, the structure of which can significantly increase the irradiation range of the light scattering patch device;

(2) The said light scattering patch device of the invention, forms the air gap and the patch on the surface of the tapered optical fiber, which can protect the tapering from the interference of complex environment inside the body, and significantly increase the stability, mechanical strength and resistance to electromagnetic interference of the optical fiber;

(3) The preparation method of the light scattering patch device of the invention, uses a single-core optical fiber fusion splicer, and sets the single-core optical fiber fusion splicer to [MM-MM/Taper splice] mode and a certain stretching distance to break a standard communication optical fiber, which ensures the size of the tip is small enough, resulting in obvious diffraction effect, and finally the tip has a large scattering angle.

BRIEF DESCRIPTION OF THE DRAWINGS

wherein the numbers in the figures are respectively represented: 1—tip, 2—tapered transition zone, 3—unstretched zone, 4—air gap, 5—patch, 6—myocardium, 7—tapered optical fiber core made by the etching method, and 8—tapered optical fiber cladding made by the etching method.

DETAILED DESCRIPTION OF THE EMBODIMENTS

Based on above mentioned method, the following embodiments are carried out for further demonstration in the present invention. It is to be understood that these embodiments are only intended to illustrate the invention and are not intended to limit the scope of the invention. In addition, it should be understood that after reading the contents described in the present invention, those technical personnel in this field can make various changes or modifications to the invention, and these equivalent forms also fall within the scope of the claims attached to the application.

The core diameter of the standard multimode optical fiber used in the said invention is 62 μm.

The single-core optical fiber fusion splicer used in this invention is Fujikura 80S+ optical fiber fusion splicer.

The structure of the poly(4-methyl-8-caprolactone) (PMCL) modified by double bonds at both ends in the invention is a PMCL with a molecular weight of 12.9 kDa (refer to *A highly stretchable bioelastomer prepared by UV curing of liquid-like poly (4-methyl-epsilon-caprolactone) precursors. J Mater Chem B* 5, 595-603 (2017).

The structure of the polyethylene glycol (PEGDA) modified by double bonds at both ends in the invention is a PEGDA with a molecular weight of 5 kDa (refer to Choi, M., et al. *Light-guiding hydrogels for cell-based sensing and optogenetic synthesis in vivo. Nat Photonics* 7, 987-994 (2013).

The structure of the polylactic acid (PLA) in the invention is a polylactic acid with a molecular weight of 63 kDa±12 kDa (refer to Nizamoglu, S., et al. *Bioabsorbable polymer optical waveguides for deep-tissue photomedicine. Nat Commun* 7, 10374 (2016).

The structure of the poly(lactic-co-glycolic acid) (PLGA) modified by double bonds at both ends in the invention is a PLGA with a molecular weight of 38 kDa-54 kDa and an acid-terminated lactide to glycolide ratio of 50:50 (refer to Nizamoglu, S., et al. *Bioabsorbable polymer optical waveguides for deep-tissue photomedicine. Nat Commun* 7, 10374 (2016).

The PDMS in the invention is Sylgard 184 purchased from Dow Corning.

Figure 1:
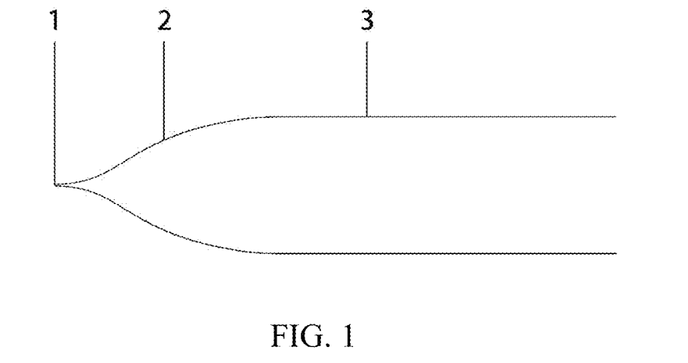
FIG. 1 is a schematic structural diagram of the tapered optical fiber of the present invention.

Using the following method to prepare a tapered optical fiber:

first, stripping a protective layer from a standard multimode optical fiber; then using a single-core optical fiber fusion splicer, and setting the single-core optical fiber fusion splicer to [MM-MM/Taper splice] mode and a stretching distance of 400 μm to break the standard communication optical fiber, obtaining the tapered optical fiber;

as shown in FIG. 1, the prepared tapered optical fiber (numbered 1A, 2A, 3A and 4A) consists of a tip 1, a tapered transition zone 2 and a partial unstretched zone 3; the specifications are shown in the table below:

| | Numbering of tapered optical fibers | | | |
|---|---|---|---|---|
| | 1A | 2A | 3A | 4A |
| Tip diameter | 1 μm | 3 μm | 2 μm | 2 μm |
| Length d of the tapered transition zone | 290 μm | 294 μm | 284 μm | 268 μm |

Figure 3:
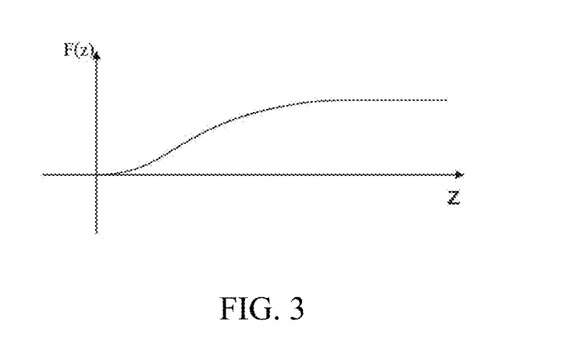
FIG. 3 is a contour fitting diagram of the cross-sectional radius F(z) of the tapered optical fiber and the distance z from the cross-section to the tip of the tapered optical fiber.

As shown in FIG. 3, a relationship between a cross-sectional radius F(z) (unit: μm) of the said tapered optical fiber and a distance z (unit: μm) from the cross-section to the tip of the tapered optical fiber satisfies a function 1, that is:

$$F(z)=62.3-56.36\times\exp(-((135.8\times(z/d)+16.18)/65.81)^2)+0.6324\times\exp(-((135.8\times(z/d)+0.5469)/0.1508)^2)+1.103\times\exp(-((135.8\times(z/d)+24.78)/-0.02043)^2)-12.1\times\exp(-((135.8\times(z/d)-13.07)/-22.32)^2);$$

The said tapered optical fibers (numbered 1A, 2A, 3A and 4A) are performed surface treatment respectively: the tapered optical fibers (numbered 1A, 2A, 3A and 4A) are fixed on the fixtures and cleaned in a plasma cleaning machine for 6 minutes, then turned over and cleaned for 6 minutes; after cleaning, the tapered optical fiber is placed in the vacuum dryer with a petri dish containing 100 μL of trichloro(1H, 1H, 2H, 2H-tridecafluoro-n-octyl) silane at the same time, and in the vacuum dryer, the tapered optical fiber and the petri dish are independent of each other and are not in direct contact with each other; vacuumize until the air pressure is less than 0.1 MPa, place at room temperature for 8 hours to complete the hydrophobic modification on the surface of the tapered optical fiber, and obtain the tapered optical fiber with hydrophobic modification on the surface (numbered 1B, 2B, 3B and 4B respectively).

Example 1C

A method of preparing the light scattering patch device, comprises the following steps:

(1) configuration of uncrosslinked polymer solution: dissolving the photoinitiator 12959 in dichloromethane, and after complete dissolution, quickly adding the uncrosslinked polymer (poly(4-methyl-ε-caprolactone) (PMCL) modified by double bonds at both ends) to stir evenly under dark conditions, and then placing the evenly stirred mixture in a vacuum dryer to remove the solvent, obtaining an uncrosslinked polymer solution; wherein the mass-to-volume ratio of the photoinitiator dissolved in the solvent is 0.01 g: 0.5 mL; wherein the mass-to-volume ratio of the uncrosslinked polymer to the solvent is 2 g: 0.5 mL; mixing sufficiently.

(2) using the pouring method to place the tapered optical fiber (numbered 1B) in the uncrosslinked polymer solution obtained in step (1) and solidify the uncrosslinked polymer solution, then pulling outwards by 10 μm along the central axis of the tapered optical fiber to form the air gap; the specific operation methods are as follows:
- (a) first taking 0.2 mL of the uncrosslinked polymer solution and drop it on a clean glass slide in the shape of a droplet (the size of the droplet can be adjusted according to the size of the prepared light scattering patch device);
- (b) carefully placing the tapered optical fiber (numbered 1B) in the center of the droplet formed by the uncrosslinked polymer solution obtained in step (a), so that the tip, the tapered transition zone and the partial unstretched zone of the tapered optical fiber are all placed inside the droplet;
- (c) placing a section of ordinary communication optical fiber (for support) on both sides of the droplet, and then covering a glass slide above the ordinary communication optical fiber, so that the parallel distance between the upper and lower glass slides is 250 μm;
- (d) using a 30 W ultraviolet lamp to irradiate the said uncrosslinked polymer solution for 5 minutes to solidify the solution to form a patch with a thickness of 250 μm;
- (e) uncovering the glass slide, cutting and trimming the shape of the patch to obtain the light scattering patch;
- (f) pulling outwards by 10 μm along the central axis of the tapered optical fiber to form the air gap; wherein before pulling the optical fiber, the tapered optical fiber and the patch are tightly attached without gaps, meanwhile, the patch is more flexible than the optical fiber, and there is a hydrophobic layer on the surface of the tapered optical fiber (numbered 1B), which can be easily pulled out of the patch; the optical fiber can only be pulled backward along the axis, after the optical fiber is pulled along the axis, the air gap is formed, and the thickness of the air gap can be controlled by controlling the pulling distance, which is d in FIG. 3.

(3) connecting the unstretched part of the tapered optical fiber after pulling that is not embedded in the patch to a light source through a standard optical fiber adapter, to form the light scattering patch device, and turning on the light source can illuminate the entire fiber patch.

Figure 2:
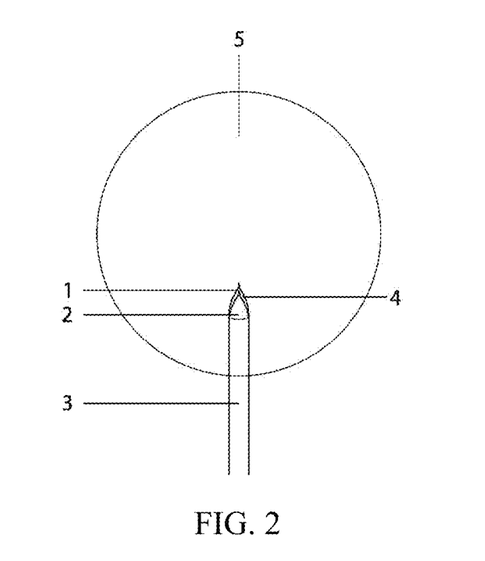
FIG. 2 is a schematic structural diagram of the light scattering patch device of the present invention.

As shown in FIG. 2, the prepared light scattering patch device comprises the patch 5, the air gap and the tapered optical fiber after hydrophobic modification on the surface; the tip 1, the tapered transition zone 2 and the partial unstretched zone 3 of the tapered optical fiber are embedded in the patch 5, and the air gap 4 is formed between the tip 1 and the tapered transition zone 2 of the tapered optical fiber and the patch; the shape of the contact surface of the air gap 4 and the patch 5 is the same as the shape of the contact surface of the air gap and the tapered optical fiber, and the contact surface of the air gap and the tapered optical fiber is the contour surface of the tip 1 and the tapered transition zone 2 of the tapered optical fiber; the maximum distance between the contact surface of the air gap and the patch, and the contact surface of the air gap and the tapered optical fiber is 6 μm; wherein the patch is a transparent patch, the refractive index of the patch is 1.49; the divergence angle of the light scattering patch device is 130°.

Comparison 1

A method of preparing the light scattering patch device, involves steps basically the same as those in Example 1C, except for that: the operation of "pulling outwards by 18 μm along the central axis of the tapered optical fiber to form the air gap" in step (2) is not performed.

Comparison 2

A method of preparing the light scattering patch device, comprises the following steps:
(1) stripping the protective layer from the same standard multimode optical fiber in Example 1C;
(2) preparing the flat-end optical fiber: using a high-precision single-core optical fiber cutting knife, cutting down a section of said standard multimode optical fiber to obtain the flat-end optical fiber;
(3) configuration of uncrosslinked polymer solution: same as Example 1C.
(4) using the pouring method to place the flat-end optical fiber obtained in step (2) in the uncrosslinked polymer solution obtained in step (3) and solidify the uncrosslinked polymer solution; the specific operation methods are as follows:
- (a) first taking 0.2 mL of the uncrosslinked polymer solution and drop it on a clean glass slide in the shape of a droplet;
- (b) carefully placing the flat-end optical fiber obtained in step (2) in the center of the droplet formed by the uncrosslinked polymer solution obtained in step (a), so that the end face of the flat-end optical fiber and a 2 mm section of optical fiber close to the end face are all placed inside the droplet;
- (c) placing a section of ordinary communication optical fiber (for support) on both sides of the droplet, and then covering a glass slide above the ordinary communication optical fiber, so that the parallel distance between the upper and lower glass slides is 250 μm (determined by the diameter of "ordinary communication optical fiber");
- (d) using a 30 W ultraviolet lamp to irradiate the said uncrosslinked polymer solution for 5 minutes to solidify the solution to form a patch with a thickness of 250 μm;
- (e) uncovering the glass slide, cutting and trimming the shape of the patch to obtain the light scattering patch;
(5) connecting the part of the flat-end optical fiber obtained in step (2) that is not embedded in the patch to a light source through a standard optical fiber adapter, to form the light scattering patch device, and turning on the light source can illuminate the entire fiber patch.

Figure 4:
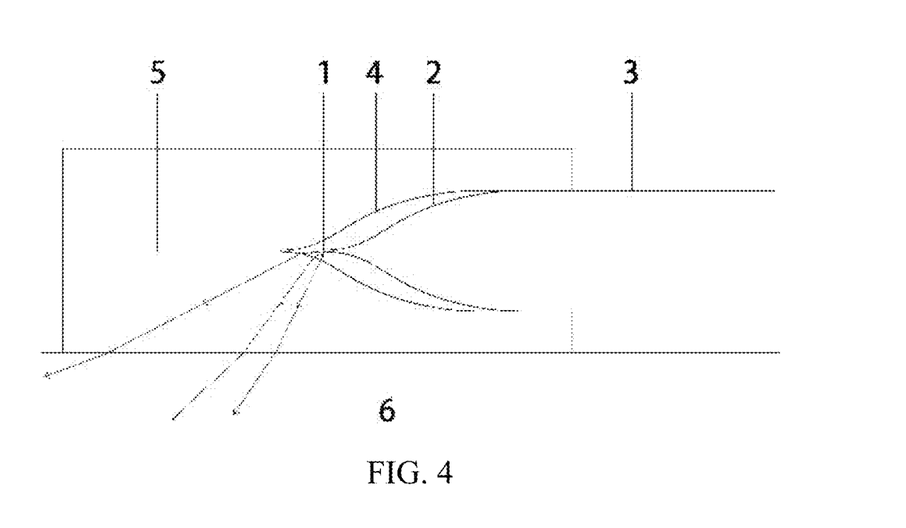
FIG. 4 is a schematic diagram (non-actual proportion) of the cross-sectional light refraction of the light scattering patch device of Example 1C.
Figure 5:
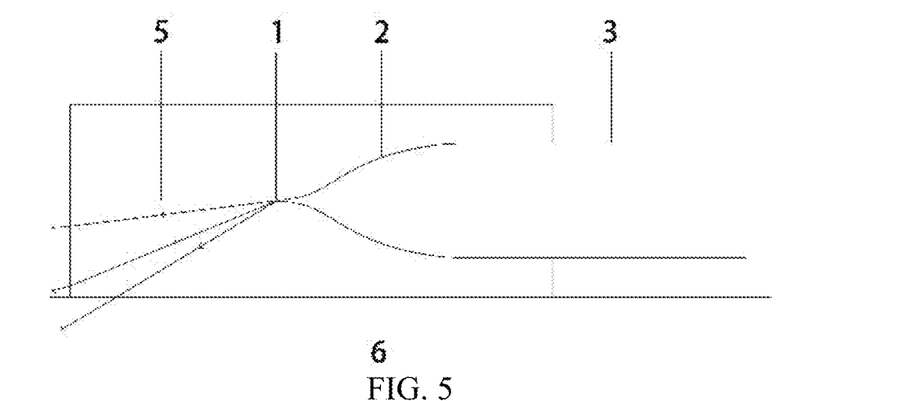
FIG. 5 is a schematic diagram (non-actual proportion) of the cross-sectional light refraction of the tapered optical fiber patch device of Comparison 1.
Figure 6:
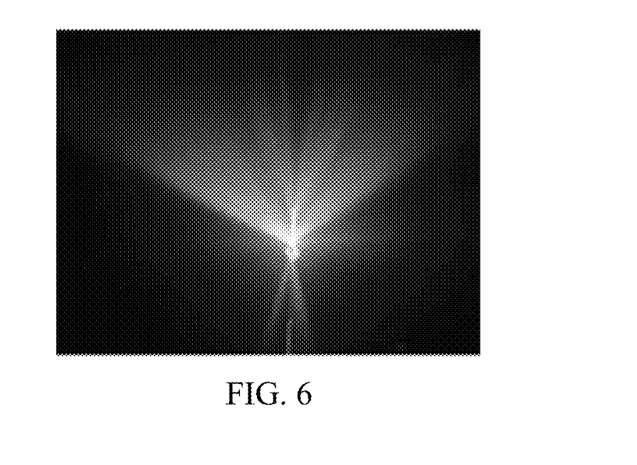
FIG. 6 is a schematic diagram of the fluorescence divergence angle of the light scattering patch device of Example 1C.
Figure 7:
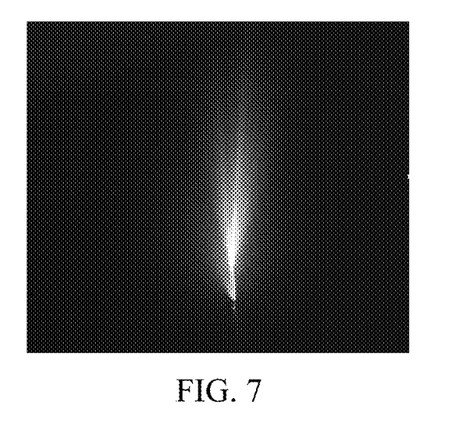
FIG. 7 is a schematic diagram of the fluorescence divergence angle of the tapered optical fiber patch device of Comparison 1.
Figure 8:
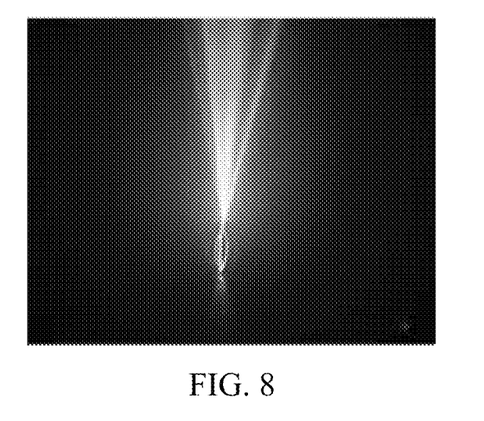
FIG. 8 is a schematic diagram of the fluorescence divergence angle of the flat-end optical fiber patch device of Comparison 2.

The schematic diagram of the cross-sectional light refraction of the prepared light scattering patch device of Example 1C and the schematic diagram of the cross-sectional light refraction of the prepared light scattering patch device of Comparison 1 are shown in FIG. 4 and FIG. 5. In Example 1C, the light emerges from the tapered optical fiber and enters the air gap, compared with Comparison 1, where the light emerges from the tapered optical fiber and directly enters the patch, the refractive index of the air is lower than that of the patch material, so that the tapered optical fiber has a larger divergence angle. Furthermore, in Example 1C, the light passing through the air gap will be refracted again at the air/patch interface, thus the divergence angle entering the myocardium 6 is further expanded. The light scattering patch devices in Example 1C, Comparison 1 and Comparison 2 are tested for fluorescence divergence angles, and their schematic diagrams of the fluorescence divergence angles are shown in FIG. 6-8, the light divergence angles of the light scattering patch devices in Comparison 1 and Comparison 2 are 20° and 40° respectively, which are both smaller than the 130° light divergence angle in Example 1C.

Example 2C

A method of preparing the light scattering patch device, comprises the following steps:
(1) configuration of uncured polymer solution: weighing the Sylgard184 PDMS prepolymer and cross-linking agent purchased from Dow Corning, and mixing evenly in a ratio of 10:1 by weight to obtain a mixed solution.
(2) using the pouring method to place the tapered optical fiber (numbered 2B) in the mixed solution of PDMS and curing agent obtained in step (1) and solidify the mixed solution, then pulling outwards by 20 µm along the central axis of the tapered optical fiber to form the air gap; the specific operation methods are as follows:
(a) first taking 0.2 mL of the mixed solution and drop it on a clean glass slide in the shape of a droplet (the size of the droplet can be adjusted according to the size of the prepared light scattering patch device);
(b) carefully placing the tapered optical fiber (numbered 2B) in the center of the droplet formed by the mixed solution obtained in step (a), so that the tip, the tapered transition zone and the partial unstretched zone part of the tapered optical fiber are all placed inside the droplet;
(c) placing a section of ordinary communication optical fiber (for support) on both sides of the droplet, and then covering a glass slide above the ordinary communication optical fiber, so that the parallel distance between the upper and lower glass slides is 250 µm;
(d) carefully transferring the system to the vacuum dryer, evacuating and heating to 80° C. for 20 minutes, to solidify the mixed solution to form a patch with a thickness of 250 µm;
(e) uncovering the glass slide, cutting and trimming the shape of the patch to obtain the light scattering patch;
(f) pulling outwards by 20 µm along the central axis of the tapered optical fiber to form the air gap;
(3) connecting the unstretched part of the tapered optical fiber after pulling that is not embedded in the patch to a light source through a standard optical fiber adapter, to form the light scattering patch device, and turning on the light source can illuminate the entire fiber patch.

The prepared light scattering patch device comprises the patch, the air gap and the tapered optical fiber after hydrophobic modification on the surface; the tip, the tapered transition zone and the partial unstretched zone of the tapered optical fiber are embedded in the patch, and the air gap is formed between the tip and the tapered transition zone of the tapered optical fiber and the patch; the shape of the contact surface of the air gap and the patch is the same as the shape of the contact surface of the air gap and the tapered optical fiber, and the contact surface of the air gap and the tapered optical fiber is the contour surface of the tip and the tapered transition zone of the tapered optical fiber; the maximum distance between the contact surface of the air gap and the patch, and the contact surface of the air gap and the tapered optical fiber is 11 µm; wherein the patch is a transparent patch, the refractive index of the patch is 1.43; the divergence angle of the light scattering patch device is 126°.

Example 3C

A method of preparing the light scattering patch device, comprises the following steps:
(1) configuration of the polymer solution: weighing PLA and dissolving in chloroform to prepare an uncured polymer solution at a concentration of 100 mg/mL.
(2) placing the tapered optical fiber (numbered 3B) in the uncured polymer solution obtained in step (1) and solidifying by solvent evaporation, then pulling outwards by 15 µm along the central axis of the tapered optical fiber to form the air gap; the specific operation methods are as follows:
(a) first taking 0.1 mL of the uncured polymer solution and drop it on a clean glass slide in the shape of a droplet (the size of the droplet can be adjusted according to the size of the prepared light scattering patch device);
(b) carefully placing the tapered optical fiber (numbered 3B) in the center of the droplet formed by the uncured polymer solution obtained in step (a), so that the tip, the tapered transition zone and the partial unstretched zone part of the tapered optical fiber are all placed inside the droplet;
(c) placing a section of ordinary communication optical fiber (for support) on both sides of the droplet, and then covering a glass slide above the ordinary communication optical fiber, so that the parallel distance between the upper and lower glass slides is 250 µm;
(d) carefully transferring the system to the vacuum dryer, and placing under vacuum for one day, after the solution is completely evaporated, a patch with a thickness of 250 µm is formed;
(e) uncovering the glass slide, cutting and trimming the shape of the patch to obtain the light scattering patch;
(f) pulling outwards by 15 µm along the central axis of the tapered optical fiber to form the air gap;
(3) connecting the unstretched part of the tapered optical fiber after pulling that is not embedded in the patch to a light source through a standard optical fiber adapter, to form the light scattering patch device, and turning on the light source can illuminate the entire fiber patch.

The prepared light scattering patch device comprises the patch, the air gap and the tapered optical fiber after hydrophobic modification on the surface; the tip, the tapered transition zone and the partial unstretched zone of the tapered optical fiber are embedded in the patch, and the air gap is formed between the tip and the tapered transition zone of the tapered optical fiber and the patch; the shape of the contact surface of the air gap and the patch is the same as the shape of the contact surface of the air gap and the tapered optical fiber, and the contact surface of the air gap and the tapered optical fiber is the contour surface of the tip and the tapered transition zone of the tapered optical fiber; the maximum distance between the contact surface of the air gap and the patch, and the contact surface of the air gap and the tapered optical fiber is 8 µm; wherein the patch is a transparent patch, the refractive index of the patch is 1.47; the divergence angle of the light scattering patch device is 128°.

Example 4C

A method of preparing the light scattering patch device, comprises the following steps:
(1) configuration of the polymer solution: weighing PLGA and dissolving in dichloromethane to prepare an uncured polymer solution at a concentration of 100 mg/mL.
(2) placing the tapered optical fiber (numbered 4B) in the uncured polymer solution obtained in step (1) and solidifying by solvent evaporation, then pulling outwards by 18 μm along the central axis of the tapered optical fiber to form the air gap; the specific operation methods are as follows:
(a) first taking 0.1 mL of the uncured polymer solution and drop it on a clean glass slide in the shape of a droplet (the size of the droplet can be adjusted according to the size of the prepared light scattering patch device);
(b) carefully placing the tapered optical fiber (numbered 4B) in the center of the droplet formed by the uncured polymer solution obtained in step (a), so that the tip, the tapered transition zone and the partial unstretched zone of the tapered optical fiber are all placed inside the droplet;
(c) placing a section of ordinary communication optical fiber (for support) on both sides of the droplet, and then covering a glass slide above the ordinary communication optical fiber, so that the parallel distance between the upper and lower glass slides is 250 μm;
(d) carefully transferring the system to the vacuum dryer, and placing under vacuum for one day, after the solution is completely evaporated, a patch with a thickness of 250 μm is formed;
(e) uncovering the glass slide, cutting and trimming the shape of the patch to obtain the light scattering patch;
(f) pulling outwards by 18 μm along the central axis of the tapered optical fiber to form the air gap;
(3) connecting the unstretched part of the tapered optical fiber after pulling that is not embedded in the patch to a light source through a standard optical fiber adapter, to form the light scattering patch device, and turning on the light source can illuminate the entire fiber patch.

The prepared light scattering patch device comprises the patch, the air gap and the tapered optical fiber after hydrophobic modification on the surface; the tip, the tapered transition zone and the partial unstretched zone of the tapered optical fiber are embedded in the patch, and the air gap is formed between the tip and the tapered transition zone of the tapered optical fiber and the patch; the shape of the contact surface of the air gap and the patch is the same as the shape of the contact surface of the air gap and the tapered optical fiber, and the contact surface of the air gap and the tapered optical fiber is the contour surface of the tip and the tapered transition zone of the tapered optical fiber; the maximum distance between the contact surface of the air gap and the patch, and the contact surface of the air gap and the tapered optical fiber is 9 μm; wherein the patch is a transparent patch, the refractive index of the patch is 1.46; the divergence angle of the light scattering patch device is 130°.

Example 5C

A method of preparing the light scattering patch device, comprises the following steps:
(1) configuration of uncrosslinked polymer solution: dissolving the photoinitiator 12959 in the solvent dichloromethane, and after complete dissolution, quickly adding the uncrosslinked polymer (polyethylene glycol (PEGDA) modified by double bonds at both ends) to stir evenly under dark conditions, and then placing the evenly stirred mixture in a vacuum dryer to remove the solvent, obtaining an uncrosslinked polymer solution; wherein the mass-to-volume ratio of the photoinitiator dissolved in the solvent is 0.01 g: 0.5 mL; wherein the mass-to-volume ratio of the uncrosslinked polymer to the solvent is 2 g: 0.5 mL; mixing sufficiently.
(2) using the pouring method to place the tapered optical fiber (numbered 3B) in the uncrosslinked polymer solution obtained in step (1) and solidify the uncrosslinked polymer solution, then pulling outwards by 17 μm along the central axis of the tapered optical fiber to form the air gap; the specific operation methods are as follows:
(a) first taking 0.2 mL of the uncrosslinked polymer solution and drop it on a clean glass slide in the shape of a droplet (the size of the droplet can be adjusted according to the size of the prepared light scattering patch device);
(b) carefully placing the tapered optical fiber (numbered 1B) in the center of the droplet formed by the uncrosslinked polymer solution obtained in step (a), so that the tip, the tapered transition zone and the partial unstretched zone of the tapered optical fiber are all placed inside the droplet;
(c) placing a section of ordinary communication optical fiber (for support) on both sides of the droplet, and then covering a glass slide above the ordinary communication optical fiber, so that the parallel distance between the upper and lower glass slides is 250 μm;
(d) using a 30 W ultraviolet lamp to irradiate the said uncrosslinked polymer solution for 5 minutes to solidify the solution to form a patch with a thickness of 250 μm;
(e) uncovering the glass slide, cutting and trimming the shape of the patch to obtain the light scattering patch;
(f) pulling outwards by 17 μm along the central axis of the tapered optical fiber to form the air gap; wherein before pulling the optical fiber, the tapered optical fiber and the patch are tightly attached without gaps, meanwhile, the patch is more flexible than the optical fiber, and there is a hydrophobic layer on the surface of the tapered optical fiber (numbered 3B), which can be easily pulled out of the patch; the optical fiber can only be pulled backward along the axis, after the optical fiber is pulled along the axis, the air gap is formed, and the thickness of the air gap can be controlled by controlling the pulling distance.
(3) connecting the unstretched part of the tapered optical fiber after pulling that is not embedded in the patch to a light source through a standard optical fiber adapter, to form the light scattering patch device, and turning on the light source can illuminate the entire fiber patch.

The prepared light scattering patch device comprises the patch, the air gap and the tapered optical fiber after hydrophobic modification on the surface; the tip, the tapered transition zone and the partial unstretched zone of the tapered optical fiber are embedded in the patch, and the air gap is formed between the tip and the tapered transition zone of the tapered optical fiber and the patch; the shape of the contact surface of the air gap and the patch is the same as the shape of the contact surface of the air gap and the tapered optical fiber, and the contact surface of the air gap and the tapered optical fiber is the contour surface of the tip and the tapered transition zone of the tapered optical fiber; the maximum distance between the contact surface of the air gap and the patch, and the contact surface of the air gap and the tapered optical fiber is 9 μm; wherein the patch is a transparent patch, the refractive index of the patch is 1.49; the divergence angle of the light scattering patch device is 128°.

What is claimed is:

1. A light scattering patch device, comprising a patch, an air gap, and a tapered optical fiber;
   wherein the patch is a transparent patch;
   wherein a refractive index of the patch is greater than a refractive index of a biological tissue;
   wherein a tip, a tapered transition zone and a partial unstretched zone of the tapered optical fiber are embedded in the patch, and the air gap is formed between the tip and the tapered transition zone of the tapered optical fiber and the patch;
   wherein a relationship between a cross-sectional radius $F(z)$ of the tapered optical fiber and a distance z from a cross-section to the tip of the tapered optical fiber satisfies a function 1; assuming that a length of the tapered transition zone is d, and the function 1 is:

$F(z)=62.3-56.36\times\exp(-((135.8\times(z/d)+16.18)/65.81)^2)+0.6324\times\exp(-((135.8\times(z/d)+0.5469)/0.1508)^2)+1.103\times\exp(-((135.8\times(z/d)+24.78)/-0.02043)^2)-12.1\times\exp(-((135.8\times(z/d)-13.07)/-22.32)^2)$; and wherein the cross-sectional radius $F(z)$, the distance z from the cross-section to the tip of the tapered optical fiber, and the length d of the tapered transition zone are all in the unit of μm.

2. The light scattering patch device of claim 1, wherein a tip diameter of the tapered optical fiber is less than 3 μm.

3. The light scattering patch device of claim 1, wherein the length d of the tapered transition zone of the tapered optical fiber is 250 μm-300 μm.

4. The light scattering patch device of claim 1, wherein a shape of a contact surface of the air gap and the patch is the same as a shape of a contact surface of the air gap and the tapered optical fiber, and the contact surface of the air gap and the tapered optical fiber is a contour surface of the tip and the tapered transition zone of the tapered optical fiber.

5. The light scattering patch device of claim 4, wherein a maximum distance between the contact surface of the air gap and the patch, and the contact surface of the air gap and the tapered optical fiber is 3-20 μm.

6. The light scattering patch device of claim 1, wherein a divergence angle of the light scattering patch device is 126°-130°.

7. A method of preparing the light scattering patch device in claim 1, comprising the following steps:
   (1) stripping a protective layer from a standard multimode optical fiber;
   (2) preparing the tapered optical fiber;
   (3) surface treatment of the tapered optical fiber: performing hydrophobic modification on the surface of the tapered optical fiber obtained in step (2);
   (4) placing the tapered optical fiber obtained in step (3) in an uncured polymer and curing the uncured polymer, and then pulling the unstretched part of the tapered optical fiber outwards by a certain distance along the central axis of the tapered optical fiber to form the air gap;
   wherein the uncured polymer is a poly(4-methyl-ε-caprolactone) modified by double bonds at both ends, a polydimethylsiloxane, a polylactic acid, a poly(lactic-co-glycolic acid) modified by double bonds at both ends, or a polyethylene glycol modified by double bonds at both ends;
   (5) connecting the unstretched part of the tapered optical fiber obtained in step (4) that is not embedded in the patch to a light source through a standard optical fiber adapter, to form the light scattering patch device.

8. The method of claim 7, wherein the specific process of step (2) is as follows: using a single-core optical fiber fusion splicer, and setting the single-core optical fiber fusion splicer to [MM-MM/Taper splice] mode and a certain stretching distance to break a standard communication optical fiber, to obtain the tapered optical fiber.

9. The method of claim 7, wherein the specific process of step (3) is as follows: placing the tapered optical fiber obtained in step (2) in a vacuum dryer under an atmosphere containing trichloro (1H, 1H, 2H, 2H-tridecafluoro-n-octyl) silane, vacuumizing until an air pressure is less than 0.1 MPa, and placing at room temperature for 8 hours.

10. The method of claim 7, wherein the certain distance in step (4) is 5-40 μm.

11. The method of claim 7, wherein a tip diameter of the tapered optical fiber is less than 3 μm.

12. The method of claim 7, wherein the length d of the tapered transition zone of the tapered optical fiber is 250 μm-300 μm.

13. The method of claim 7, wherein a shape of a contact surface of the air gap and the patch is the same as a shape of a contact surface of the air gap and the tapered optical fiber, and the contact surface of the air gap and the tapered optical fiber is a contour surface of the tip and the tapered transition zone of the tapered optical fiber.

14. The method of claim 13, wherein a maximum distance between the contact surface of the air gap and the patch, and the contact surface of the air gap and the tapered optical fiber is 3-20 μm.

15. The method of claim 7, wherein a divergence angle of the light scattering patch device is 126°-130°.

* * * * *